(12) United States Patent
Anhauser et al.

(10) Patent No.: US 6,315,854 B1
(45) Date of Patent: Nov. 13, 2001

(54) TRANSDERMAL THERAPEUTIC PLASTER

(75) Inventors: Dieter Anhauser, Melsbach; Lothar Deurer, Koblenz; Thomas Hille, Neuwied; Peter Steinborn, Neuwied, all of (DE)

(73) Assignee: LTS Lohmann Therapie-Systeme GmbH & Co. KG, Neuwied (DE)

( * ) Notice: Subject to any disclaimer, the term of this patent is extended or adjusted under 35 U.S.C. 154(b) by 1364 days.

(21) Appl. No.: 08/531,890

(22) Filed: Sep. 22, 1995

Related U.S. Application Data (6362) Continuation of application No. 08/122,496, filed as application No. PCT/EP92/00513 on Mar. 9, 1992, now abandoned.

(30) Foreign Application Priority Data

Mar. 27, 1991 (DE) .................................................. 41 10 027

(51) Int. Cl.⁷ .......................... B32B 31/10; B32B 31/18; A61M 35/00
(52) U.S. Cl. .......................... 156/267; 156/250; 156/270; 156/301
(58) Field of Search .................................... 156/145, 152, 156/250, 267, 268, 269, 270, 324, 300, 301, 248, 249; 424/448, 449; 604/307

(56) References Cited

U.S. PATENT DOCUMENTS

| | | | | |
|---|---|---|---|---|
| 2,703,083 | * | 3/1955 | Gross | 156/248 X |
| 2,862,846 | * | 12/1958 | Blackford et al. | 156/249 |
| 3,245,855 | * | 4/1966 | Stenvall | 156/152 |
| 4,556,441 | * | 12/1985 | Faasse, Jr. | 156/267 X |
| 4,614,076 | | 9/1986 | Rathemacher | |
| 4,638,043 | * | 1/1987 | Szycher et al. | 424/449 X |
| 4,704,119 | * | 11/1987 | Shaw et al. | 424/448 |
| 4,708,716 | * | 11/1987 | Sibalis | 424/449 X |
| 4,758,434 | * | 7/1988 | Kydonieus et al. | 424/449 |
| 4,844,903 | * | 7/1989 | Seth | 424/449 X |
| 4,867,821 | * | 9/1989 | Morgan | 156/152 |
| 4,994,267 | * | 2/1991 | Sablotsky | 424/448 X |
| 5,112,618 | * | 5/1992 | Cartmell et al. | 424/449 X |
| 5,126,144 | * | 6/1992 | Jaeger et al. | 424/449 X |
| 5,133,970 | * | 7/1992 | Petereit et al. | 424/449 X |
| 5,176,915 | * | 1/1993 | Hoffmann | 424/448 X |
| 5,268,179 | * | 12/1993 | Rudella | 424/449 |

FOREIGN PATENT DOCUMENTS

| | | |
|---|---|---|
| 3315272 | 10/1984 | (DE) . |
| 3629304 | 3/1988 | (DE) . |
| 3222800 | 3/1989 | (DE) . |
| 242827 | 10/1987 | (EP) . |
| 335231 | 10/1989 | (EP) . |

OTHER PUBLICATIONS

Heilmann, Klaus: "Therapeutic Systems—Concept and Realization of Programmed Administration of Drugs," *Ferdinand Enke Verlag Stuttgart*, 4th Ed., 1984, p. 26.

* cited by examiner

*Primary Examiner*—Curtis Mayes
(74) *Attorney, Agent, or Firm*—Collard & Roe, PC

(57) ABSTRACT

A process for continuously manufacturing transdermal therapeutic patches having a backing layer, a pressure-sensitive adhesive drug reservoir layer, and a removable protective layer, whereby loss of active substances during fabrication of the patches is minimized, said process being characterized in that, in a tape-like laminate having a pressure-sensitive adhesive backing layer (1) and a removable protective layer (3), single quadrangular pressure-sensitive adhesive drug reservoir sections (2) are inserted one after the other in the longitudinal direction between the layers (2,3); the clearance between said drug reservoir sections remains constant in the longitudinal direction; their width is calculated such that the backing layer (1) and the removable protective layer (3) project beyond both sides of said sections; the pressure-sensitive adhesive backing layer (1) is first cut by punching in such a way that the punching line (1*a*) surrounds the individual drug reservoir sections (2) at an evident distance from their outer dimensions; the the resulting lattice-type refuse of the drug-free pressure-sensitive adhesive backing layer (1) is removed; and subsequently the protective layer (3) is cut in the resultant spaces between the drug reservoir sections (2).

3 Claims, 1 Drawing Sheet

TRANSDERMAL THERAPEUTIC PLASTER

Figure 1:
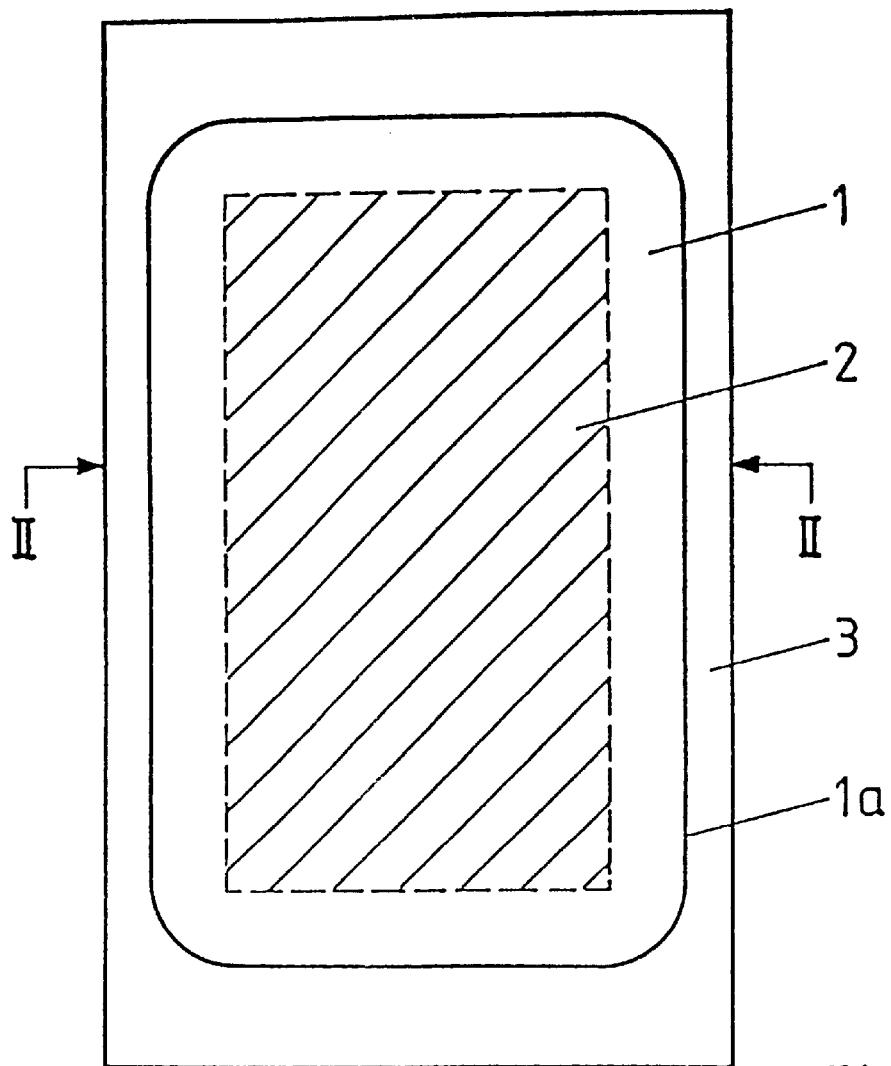

This is a continuation of copending application(s) Ser. No. 08/122,496 filed on Oct. 28, 1993, now abandoned, which is the national stage of International Application PCT/EP92/00513 filed on Mar. 9, 1992 and which designated the U.S.

The present invention relates to a process for the continuous production of transdermal therapeutic patches having a backing layer, a pressure-sensitive adhesive drug-reservoir-layer, and a removable protective layer, wherein the loss of active substance caused by production is minimized.

A transdermal therapeutic patch (hereinafter abbreviated to TT-patch) is a dosage form which is to be applied to the skin and looks like a traditional plaster, it contains drugs which are to be released via the skin and is known as "Transdermal Therapeutic System". A therapeutic system may contain one or more drugs which are continuously released at a predetermined rate over a defined period of time to a defined site of application ("Heilmann, Klaus: Therapeutische Systeme—Konzept und Realisation programmierter Arzneiverabreichung"["Therapeutic Systems—Concept and Realization of Programmed Administration of Drugs"], 4th edition, Ferdinand Enke Verlag Stuttgart, 1984, page 26).

The therapeutic use of such forms of medication is known. In general these forms of administration are composed of several layers and—in the most simple case—consist of a backing layer, a self-adhesive active substance reservoir, and a protective layer which is to be removed prior to application. For obvious reasons, the design of choice for TT-patches is a round or geometric shape having rounded edges. Processes suitable for the series production of TT-patches must ensure a uniform drug content in the individual patches. These processes should be so simple that production can be carried out economically efficient, i.e., above all the loss of active substance must be kept as low as possible.

Such processes are known. A medicinal release system for administering an active substance via the skin is described in German Patent No. 32 22 800; it consists of a support, an adjacent reservoir containing an active substance and a liquid, a Theological agent, such as cellulose, a polysaccharide, or a silicon compound, and a membrane bordering the reservoir for determining the release rate of the active substance from the system. This system exhibits several shortcomings. For example, the individual dosage by spreading a liquid preparation on a defined area and at a defined thickness is very difficult, and a loss of active substances must be expected during production since single pieces have to be eliminated due to diverging drug loads. In addition, if the membrane gets damaged, abrupt drug release must be expected and this might result in fatal consequences to the patient.

German Patent No. 36 29 304 describes a therapeutic system consisting of a drug depot which is covered by a backing layer and contains a liquid active substance or a liquid drug preparation and one or more adjuvants having supporting and distributing functions being completely surrounded by a matrix, a matrix controlling the active substance release, and a pressure-sensitive adhesive fixation facility. The shortcoming of this system is the fact that only liquid drugs or drug preparations may be used and the complicated dosage thereof makes production without drug losses nearly impossible.

In the process for the manufacture of TT-plasters described in German Patent No. 33 15 272 pressure-sensitive adhesive layers containing active substances are applied to a protective layer which is impermeable to the active substance and covered with a likewise impermeable backing layer. Except for the removable protective layer, all layers are cut through when the individual plasters are punched out. The loss of active substance may be considerable due to the refuse remaining between the individual plasters; in this connection it must be considered that the active substances used in transdermal therapy represent hazardous waste.

It is accordingly the object of the present invention to provide a continuous process for manufacturing TT-patches wherein losses of active substance are prevented to a large extent and which does not involve a great deal of technical expenditure. In this process the drug reservoir is produced by known coating techniques, such as coating with drug-containing solutions of pressure-sensitive adhesives, aqueous pressure-sensitive adhesive dispersions, or molten pressure-sensitive adhesive masses.

The drug-containing reservoir consisting of a drug-containing pressure-sensitive adhesive layer and a backing layer is cut into squares or rectangles by cross cutting and slitting the coating material. The quadrangular reservoirs, with the layer formed by the drug-containing pressure-sensitive adhesive, are centrically placed at the desired distances on a removable protective layer projecting in all directions. Subsequently, the protective layer is covered with a backing layer coated with a drug-free pressure-sensitive adhesive. The backing layer is considerably wider than the active substance reservoirs, however, it need not be as wide as the protective layer. Thus the reservoir's backing layer acts as a barrier layer preventing the drug from migrating into the drug-free pressure-sensitive adhesive layer.

After coating, the laminate consisting of a removable film and the drug-containing pressure-sensitive adhesive layer, is covered with a flexible film, which film will serve as a barrier layer in the final product. Then the laminate of removable film, drug-containing pressure-sensitive adhesive layer and flexible film is cut into narrow rolls. By cutting in a transverse direction to the tape and stripping the removable film, quadrangular laminates are obtained consisting of a drug-containing pressure-sensitive adhesive layer (the drug reservoir) and a flexible film. Said quadrangular laminates, with the drug-containing pressure-sensitive adhesive layer, are centrically placed at the desired distances on a removable protective layer projecting at all sides. Subsequently, the protective layer is covered with a backing layer coated with a drug-free pressure-sensitive adhesive, which backing layer is considerably wider than the drug reservoirs, but need not be as wide as the protective layer. Thus the flexible film on the drug reservoir acts as a barrier layer, preventing the drug from migrating into the drug-free pressure-sensitive adhesive layer.

The subsequent punching is carried out along the outlines running at a distance of the drug reservoirs. In this process, the pressure-sensitive adhesive backing layer is cut through whereas the removable protective layer remains intact. The lattice remaining between the individual patches is drug-free waste. The TT-patches according to the present invention are obtained by cutting the protective layer between the reservoirs, the cuts being made vertically with respect to the longitudinal direction.

The TT-patch according to the present invention exhibits a multi-layer structure. The backing layer may consist of flexible or non-flexible material. Polymeric films or metal foils, such as aluminium foils alone or coated with a polymeric substrate, may be used for the production thereof. Textile fabrics may also be used, provided that they are impermeable to the components of the drug-free pressure-sensitive adhesive layer which may optionally consist of a plasticizer or a tackifier. In a preferred embodiment of the present invention, the backing layer is an aluminized foil.

The pressure-sensitive adhesive layer consists of a polymeric matrix with a base polymer and, optionally, common additives. Examples of suitable polymers comprise silicones, rubber, rubber-like synthetic homo-polymers, copolymers or block polymers, polyacrylates and the copolymers thereof, and esters of hydrogenated colophony. In principle all polymers are suitable which are used in the production of pressure-sensitive adhesives and are physiologically acceptable. Particularly preferred are those consisting of acrylate and/or methacrylate when present as block copolymers based on styrene and 1,3-dienes, polyisobutylenes, or polymers and copolymers. Linear styrene styrene-isoprene-styrene block copolymers are preferably used among the block copolymers based on styrene and 1,3-dienes.

Examples of preferred polymers based on acrylate include acrylate copolymers of 2-ethyl hexyl acrylate, vinyl acetate, and acrylic acid with and without titanium chelate esters. The particularly preferred esters of hydrogenated colophony are the methyl and glycerol esters thereof.

The kind of potential plasticizers and tackifiers used as additives depends on the employed polymer. Suitable physiologically acceptable substances are known. The permanent contact to the skin must be ensured by the self-adhesiveness of the pressure-sensitive adhesive layer alone. It may be applied to the backing layer by means of the hot-melt-process, as a solution or as dispersion pressure-sensitive adhesive.

The barrier layer preferably consists of the same materials as the backing layer. It serves to prevent the drug or plasticizer from diffusing out of the reservoir into the drug-free pressure-sensitive adhesive layer during storage of the systems.

The reservoir layer consists of a self-adhesive polymeric matrix and the drug. The polymer matrix consists of a base polymer and, optionally, conventional additives. Selection of the basic polymer is determined by the chemical and physical properties of the active substance. The polymers may be selected from the same group as those of the drug-free adhesive layer.

Substances causing a local or systemic action when applied to the skin, either without or with an absorbifacient, are used as drugs.

Examples of substances having a local action include anhydrotics, fungicides, bactericides, and bacteriostats.

Substances having a systemic action, for example, are antibiotics, hormones, antipyretics, antidiabetics, coronary vasodilators, cardio-active glycosides, spasmolytics, antihypertensives, psychopharmaceuticals, migraine analgesics, corticoids, analgesics, contraceptives, antirheumatics, anticholinergics, sympatholytic drugs, sympathomimetics, vasodilators, anticoagulants, and antiarrhythmics.

Potential additives used in dependence on the polymer and drug, for example, are plasticizers, tackifiers, stabilizers, carriers, diffusion and penetration controlling additives, or fillers. The suitable physiologically acceptable substances are known. The self-adhesiveness of the reservoir layer has to ensure a permanent contact to the skin. As mentioned above, it is only a sufficient adhesive strength of the reservoir layer that ensures safe adherence of the reservoir layer, since this is the precondition for a sufficient drug release from the system. It cannot be compensated by the drug-free pressure-sensitive adhesive edge.

The protective layer on the reservoir layer, which is to be removed prior to application, may, for example, consist of the same materials as those used for the production of the backing layer. However, they have to be rendered removable, e.g., by a silicone treatment. Other removable protective layers, for example, are polytetrafluoroethylene, treated paper, cellophane, polyvinyl chloride, and the like.

The present invention will be illustrated by the accompanying drawings and an embodiment. In the drawings FIG. 1 shows a plan view of the TT-patch according to the present invention, FIG. 2 is a sectional drawing along line II—II of the TT-patch of FIG. 1.

FIG. 1 is a schematic top drawing of the TT-patch according to the present invention. The backing layer 1 which is coated with a drug-free pressure-sensitive adhesive is placed on the removable protective layer 3, in this case of a rectangular shape. The backing layer 1 is a rectangle with rounded edges. Other shapes are possible. The punching line 1a outlines the shape of the backing layer 1. It runs outside of the laminate 2 in order to prevent loss of drug during punching.

The outlines of the hidden rectangular laminate 2 which consists of the reservoir 6 and the barrier layer 5 can be recognized within the backing layer 1. According to the present invention, the backing layer 1 projects beyond the laminate 2 at all sides. The laminate 2 is of quadrangular shape, since it is obtained by cross cutting the previous form which is wound up to form a narrow roll. The choice of the cutting direction, relative to the running direction, determines whether a rectangle, square, parallelogram, or a trapezoid results during the cutting procedure. The rectangular form is preferred. When the reservoir is cut it must be noticed that drug losses can only be prevented effectively, if the laminate 2 exhibits the form of a quadrangle.

Figure 2:
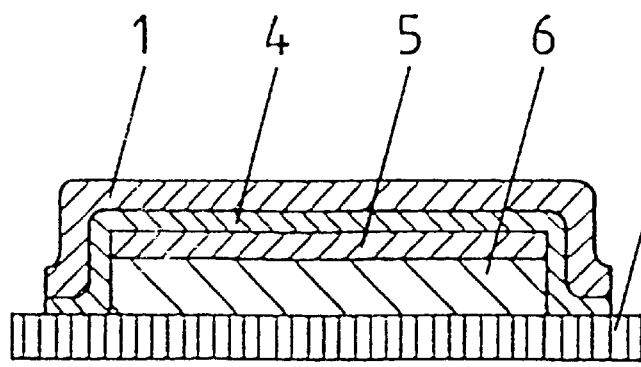

FIG. 2 is a cross-section along II—II of FIG. 1. For the purpose of clarity the layer thicknesses are shown in an exaggerated manner. The laminate 2 consists of the reservoir 6 and the barrier layer 5 and is positioned on the protective layer 3; the barrier layer 5 separates the reservoir 6 from the drug-free pressure-sensitive adhesive layer 4 covering the backing layer 1. As can be seen, the backing layer 1 and the drugfree pressure-sensitive adhesive layer 4 project beyond all sides of the laminate 2.

EXAMPLE

For the production of the reservoir laminate, which is preferably prepared in narrow rolls, 3.45 kg of a 47.83% wt. polyacrylate solution of a self-crosslinking acrylate copolymer of 2-ethyl hexyl acrylate, vinyl acetate, and acrylic acid (solvent:ethyl acetate:heptane:isopropanol:toluene:acetyl acetone at a ratio of 37:26:26:4:1) are intimately mixed for one hour with 0.25 kg of a polyethylated glycerol with $C_8/C_{10}$ ethoxy groups the free hydroxyl groups of which being partially esterified with caprylic/capric acids, 0.5 kg methanol, 0.35 kg glutaric acid monomethyl ester, 0.125 kg of a polymethacrylate based on a copolymer of dimethylaminoethyl methacrylate and neutral methacrylates, and 0.25 kg buprenorphine base.

Subsequently the mixture is applied to a transparent, 420 mm wide polyester film having a thickness of 50 μgm so that the weight per area of the dried adhesive layer is in the order of 120 g/m². The polyester film rendered removable by siliconization serves as an intermediate cover. After drying, a polyester sheet (thickness 36 μm, width 420 mm) being impermeable to the active substance and, at a later stage, will serve as barrier layer is applied. After cutting the laminate 2 in the longitudinal direction at distances of 70 mm the laminate consisting of intermediate cover, reservoir layer, and barrier layer is present in the form of narrow rolls.

For the production of the drug-free adhesive layer 23.32 kg of a 47.83% wt. polyacrylate solution of a self-crosslinking acrylate copolymer of 2-ethyl hexyl acrylate, vinylacetate, and acrylic acid (solvent:ethyl acetate:heptane:isopropanol:toluene:acetyl acetone=37:26:26:4:1) are mixed for 10 minutes with 0.6 kg 2-octyl dodecanol and applied to a siliconized transparent polyester sheet (thickness 100 μm, width 406 mm) in such a way that the weight per area of the dried adhesive layer is in the order of 120 g/m².

After drying, the adhesive layer is covered with a cuticolor polyester film having a thickness of 23 μm and a width of 406 mm which, at a later stage, will serve as the backing layer of the system. Parallel cutting in the longitudinal direction at a distance of 90 mm each results in the drug-free adhesive laminate consisting of intermediate cover, drug-free adhesive layer, and backing layer, present in the form of narrow rolls, too.

A siliconized 100 μm polyester film is used to form narrow rolls 90 mm in width for the protective layer.

A narrow roll of the reservoir laminate consisting of barrier layer, reservoir layer, and intermediate cover is placed in a dispenser (unroll stand) provided with a suitable known device in such a manner that the intermediate cover lies underneath. The 90 mm wide and 100 μm thick polyester film designated to form the protective layer is running directly below the device in vertical direction of the reservoir laminate with its siliconized side facing upwardly. The barrier layer (5) and the reservoir layer (6) forming a pressure-sensitive adhesive drug reservoir section (2) are cut at distances of 35.7 mm in vertical direction of the running movement by means of a suitable cutting device, the intermediate cover not being cut. The intermediate cover is pulled in acute angle over the dispenser edge of the known device. The rectangles (2) of reservoir layer (6) and barrier layer (5) having an edge length of 70 mm×35.7 mm are centrically placed on the siliconized polyester film directly running below the dispenser edge. Since the siliconized polyester sheet is running continuously and the rectangles (2) are dispensed in intervals, a distance between the individual rectangles (2) of 20 mm results.

In a second laminating station, the laminate of backing layer (1), drug-free adhesive layer (4), and intermediate cover, which is present in the form of narrow rolls, is inserted in such a manner that the intermediate cover lies at the bottom. The intermediate cover is pulled off mechanically; from the top, the remaining laminate of backing layer (1) and drug-free adhesive layer (4) is placed with its edges in straight line and in parallel to the running direction on the rectangles (2) located on the protective layer (3); winding up follows. Thus the TT-patches according to the present invention are provided in the form of a narrow roll and merely have to be isolated yet.

For this purpose, the backing layer (1) without the protective layer (5) is cut by means of a punching die having the shape of a rectangle with rounded edges and an edge length of 90 mm×50 mm in such a way that the rectangle of barrier layer (5) and reservoir layer (6) is positioned in the center of the punched-out surface. The drug-free lattice lying between the systems is removed as refuse. The TT-patches according to the present invention are obtained by cutting the protective layer (3) between the individual systems in vertical direction of the tape direction. They are packed subsequently.

What is claimed is:

1. A process for the continuous production of transdermal therapeutic patches having a backing layer, a pressure-sensitive adhesive drug-reservoir-section and a removable protective layer, in which the loss of drug during fabrication is minimized, comprising the steps of providing a backing layer coated with a drug-free pressure-sensitive adhesive, wherein said backing layer is fed from a roll;

and further providing a removable protective layer which is fed from a roll;

placing individual quadrangular pressure-sensitive adhesive drug-reservoir sections lengthwise one after the other on said protective layer and covering the protective layer with said backing layer, and the clearance between said drug-reservoir sections in longitudinal direction remaining constant and the width thereof being dimensioned such that said backing layer and said removable protective layer project beyond said drug-reservoir-section at all sides thereof, whereafter the pressure-sensitive adhesive drug-free backing layer is cut by punching in such a manner that the punching line surrounds the external dimensions of the individual drug reservoir sections, removing the resulting latticed refuse of the drug-free pressure-sensitive adhesive backing layer, and then cutting the protective layer in the resultant spaces between the drug-reservoir-sections.

2. The process according to claim 1, wherein prior to placing the pressure-sensitive adhesive drug reservoir sections on said protective layer and covering said protective layer with said backing layer, that side of said pressure-sensitive adhesive reservoir section facing said backing layer is covered with a barrier layer being impermeable to active substances.

3. A process for the continuous production of transdermal therapeutic patches having a backing layer, a pressure-sensitive adhesive drug-reservoir-section and a removable protective layer, in which the loss of drug during fabrication is minimized, comprising the steps of providing a backing layer coated with a drug-free pressure-sensitive adhesive, wherein said backing layer is fed from a roll;

and further providing a removable protective layer which is fed from a roll;

placing individual quadrangular pressure-sensitive adhesive drug-reservoir sections lengthwise one after the other on said protective layer, covering the protective layer with said backing layer and the clearance between said drug-reservoir sections in longitudinal direction remaining constant and the width thereof being dimensioned such that said backing layer and said removable protective layer project beyond said drug-reservoir section at all sides thereof, whereafter the pressure-sensitive adhesive drug-free backing layer is cut by punching in such a manner that the punching line surrounds the external dimensions of the individual drug reservoir sections; wherein said drug-reservoir-section comprises a pressure-sensitive drug-reservoir layer having a barrier layer in contact with said drug-reservoir layer;

removing the resulting latticed refuse of the drug-free pressure-sensitive adhesive backing layer, and then cutting the protective layer in the resultant spaces between the drug-reservoir-sections.

* * * * *